(12) United States Patent
Dycus (10) Patent No.: US 8,192,444 B2
(45) Date of Patent: Jun. 5, 2012

(54) UTERINE SEALER

(75) Inventor: Sean T. Dycus, Broomfield, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 615 days.

(21) Appl. No.: 12/352,931

(22) Filed: Jan. 13, 2009

(65) Prior Publication Data

US 2009/0182329 A1   Jul. 16, 2009

Related U.S. Application Data

(60) Provisional application No. 61/021,582, filed on Jan. 16, 2008.

(51) Int. Cl.
*A61B 18/18* (2006.01)
*A61B 17/42* (2006.01)
*A61B 17/46* (2006.01)
*A61D 1/10* (2006.01)
*A61D 1/06* (2006.01)

(52) U.S. Cl. ........... 606/113; 606/47; 606/119; 606/135

(58) Field of Classification Search .............. 606/45–47, 606/119, 135–137, 113
See application file for complete search history.

(56) References Cited

U.S. PATENT DOCUMENTS

| | | | |
|---|---|---|---|
| 2,054,149 A | 9/1936 | Wappler | |
| 4,493,320 A | 1/1985 | Treat | |
| 4,503,855 A | 3/1985 | Maslanka | |
| 5,078,716 A | 1/1992 | Doll | |
| 5,520,698 A | 5/1996 | Koh | |
| 5,558,672 A | 9/1996 | Edwards et al. | |
| 5,562,720 A | 10/1996 | Stern et al. | |
| 5,643,285 A | 7/1997 | Rowden et al. | |
| 5,840,077 A | 11/1998 | Rowden et al. | |
| 5,902,300 A * | 5/1999 | Hahnen et al. | 606/46 |
| 6,221,039 B1 | 4/2001 | Durgin et al. | |
| 6,508,815 B1 | 1/2003 | Strul et al. | |
| 6,972,017 B2 | 12/2005 | Smith et al. | |
| 7,135,018 B2 * | 11/2006 | Ryan et al. | 606/48 |
| 2005/0125006 A1 * | 6/2005 | Nady | 606/119 |

(Continued)

FOREIGN PATENT DOCUMENTS

CA         2104423       2/1994

(Continued)

OTHER PUBLICATIONS

U.S. Appl. No. 12/336,970, filed Dec. 17, 2008.

(Continued)

*Primary Examiner* — Nicholas Lucchesi
*Assistant Examiner* — Rebecca E Eisenberg (57) ABSTRACT

The present disclosure relates to a device for use with an operating end of a uterine manipulator for sealing tissue that includes a shaft having a handle at an operating end thereof and a ring-like snare at a distal end thereof. The handle has an actuator operable to selectively cinch the snare from a first configuration to a second configuration. An electrode is operably coupled to an the snare and is connected to an energy source to energize tissue to create a tissue seal. The shaft is positionable within a surgical cavity such that the snare encircles tissue and operably engages and cinches the operating end of the uterine manipulator under a sealing pressure. Energy is applied to the electrode to seal the tissue disposed between the uterine manipulator and the snare under a working pressure. The tissue may then be resected and removed from the body.

19 Claims, 9 Drawing Sheets

U.S. PATENT DOCUMENTS

| | | | |
|---|---|---|---|
| 2007/0078459 | A1 | 4/2007 | Johnson et al. |
| 2007/0142844 | A1* | 6/2007 | Kotmel et al. ............... 606/119 |
| 2007/0198011 | A1 | 8/2007 | Sugita |
| 2007/0213706 | A1* | 9/2007 | Dumbauld et al. ............ 606/45 |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0467501 | 1/1992 |
| EP | 1159926 | 12/2001 |
| EP | 1769766 | 4/2007 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 93/21845 | 11/1993 |
| WO | WO 96/13218 | 5/1996 |

OTHER PUBLICATIONS

U.S. Appl. No. 12/399,614, filed Mar. 6, 2009.
U.S. Appl. No. 12/195,624, filed Aug. 21, 2008.
U.S. Appl. No. 12/367,791, filed Feb. 9, 2009.
U.S. Appl. No. 12/361,367, filed Jan. 28, 2009.
U.S. Appl. No. 12/361,375, filed Jan. 28, 2009.
U.S. Appl. No. 12/400,901, filed Mar. 10, 2009.
U.S. Appl. No. 12/176,679, filed Jul. 21, 2008.
U.S. Appl. No. 12/237,515, filed Sep. 25, 2008.
U.S. Appl. No. 12/204,976, filed Sep. 5, 2008.
U.S. Appl. No. 12/192,170, filed Aug. 15, 2008.
U.S. Appl. No. 12/233,157, filed Sep. 18, 2008.
U.S. Appl. No. 12/237,582, filed Sep. 25, 2008.
U.S. Appl. No. 12/210,598, filed Sep. 15, 2008.
U.S. Appl. No. 12/200,154, filed Aug. 28, 2008.
U.S. Appl. No. 12/211,205, filed Sep. 16, 2008.
U.S. Appl. No. 12/244,873, filed Oct. 3, 2008.
U.S. Appl. No. 12/246,553, filed Oct. 7, 2008.
U.S. Appl. No. 12/248,115, filed Oct. 9, 2008.
U.S. Appl. No. 12/353,474, filed Jan. 14, 2009.
U.S. Appl. No. 12/353,470, filed Jan. 14, 2009.
U.S. Appl. No. 12/352,942, filed Jan. 13, 2009.
U.S. Appl. No. 12/237,556, filed Sep. 25, 2008.
U.S. Appl. No. 12/411,542, filed Mar. 26, 2009.
U.S. Appl. No. 12/248,104, filed Oct. 9, 2008.
U.S. Appl. No. 12/254,123, filed Oct. 20, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/236,666, filed Sep. 24, 2008.
U.S. Appl. No. 12/192,189, filed Aug. 15, 2008.
U.S. Appl. No. 12/192,243, filed Aug. 15, 2008.
U.S. Appl. No. 12/331,643, filed Dec. 10, 2008.
U.S. Appl. No. 12/353,466, filed Jan. 14, 2009.
U.S. Appl. No. 12/363,086, filed Jan. 30, 2009.
U.S. Appl. No. 12/419,729, filed Apr. 7, 2009.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; Vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'L Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'L Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report Ep 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report Ep 04027705.5 dated Feb. 3, 2005.
Int'l Search Report Ep 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Intl Search Report PCT/US08/61498 dated Sep. 22, 2008.
Int'l Search Report PCT/US09/032690 dated Jun. 16, 2009.

* cited by examiner

UTERINE SEALER

CROSS-REFERENCE TO RELATED APPLICATIONS

This application claims the benefit of priority to U.S. Provisional Application Ser. No. 61/021,582 entitled "UTERINE SEALER" filed Jan. 16, 2008 by Sean T. Dycus, which is incorporated by reference herein.

BACKGROUND

Technical Field

1. Field of the Invention

The present disclosure relates to medical instrumentation, and more particularly to a device for use with a uterine manipulator to facilitate laparoscopically sealing and resecting cervical and uterine tissue.

2. State of the Art

Typically a uterine manipulator is currently deemed necessary by practitioners for many laparoscopic procedures involving the female pelvic organs (e.g., uterus, tubes, ovaries, etc.) as surgery without a uterine manipulator may be more time consuming. For example, laparoscopies in which a uterine manipulator has substantial utility include: tubal ligations; diagnostic laparoscopies for evaluating pelvic pain and infertility; treatment of endometriosis, removal of pelvic scars (adhesions) involving the uterus, fallopian tubes and ovaries; treatment of ectopic pregnancy; removal of uterine fibroids; removal of ovarian cysts; removal of ovaries; tubal repair; laparoscopic hysterectomy, laparoscopic repair of pelvic bowel or bladder; sampling of pelvic lymph nodes; "tying up" the bladder to prevent urine loss; and biopsy of pelvic masses.

Most state of the art manipulators are semi-rigid instruments having a manipulating handle that is grasped outside the vagina and a working end which operatively engages one or more organs in the uterus. Exposure of the vital regions of the pelvis is difficult and surgery with open or laparoscopic instruments is often difficult and, in some cases, suboptimal. For example, the uterus typically can only be safely elevated about 45° from the vaginal axis, or lowered 10°-15° from the same and movement to the right or left is minimal, at most, due to the pelvic bones. Once the uterine organ is in place, the surgeon can perform one of the above mentioned surgical procedures.

One of the most significant complications of any surgical procedure involving the uterus, e.g., partial or complete hysterectomy, is the risk of persistent and excessive bleeding due to the large blood supply in the pelvic region and blood-laden organs. For example, the open technique carries increased risk of hemorrhage due to the need to move the intestinal organs and bladder in order to reach the reproductive organs and to search for collateral damage from endometriosis or cancer. However, an open hysterectomy provides the most effective way to ensure complete removal of the reproductive system as well as providing a wide opening for visual inspection of the abdominal cavity.

Some hysterectomies are done through the manipulation of the cervix and/or uterus utilizing a uterine manipulator and resection of the cervix (total hysterectomy) or uterus (supracervical) utilizing one or more laparoscopic instruments inserted through the navel (or other body access made with a trocar). Even though these techniques tend to reduce the recovery time in most instances, there remains the risk of excessive and persistent bleeding which in this instance is not easily controlled due to the blood-laden nature of the cervix and the remote nature of the laparoscopy. As a result, if excessive bleeding does occur, the surgeon may need to convert the procedure to an open procedure to control the bleeding essentially abandoning the benefits of the laparoscopic procedure.

SUMMARY

The present disclosure relates to a device for use with an operating end of a uterine manipulator for sealing uterine tissue and includes a shaft having a handle at an operating end thereof and a ring-like snare at a distal end thereof. The handle includes an actuator operable to selectively cinch the ring-like snare from a first configuration having a first diameter to at least one subsequent configuration having a second diameter. An electrode is operably coupled to an inner peripheral surface of the ring-like snare and is adapted to connect to an electrical energy source to energize uterine tissue to create a tissue seal. The shaft is selectively positionable within a surgical cavity such that the ring-like snare encircles uterine tissue and operably engages and cinches the operating end of the uterine manipulator under a sealing pressure. Electrosurgical energy is applied to the electrode to seal the uterine tissue disposed between the uterine manipulator and the ring-like snare.

In one embodiment according to the present disclosure, the electrode is further energized after the successful completion of the tissue seal to resect/or cut the uterine tissue along the tissue seal. In another embodiment, the device includes a second electrode that is adapted to connect to the electrical energy source, the second electrode is energized after the successful completion of the tissue seal to resect the tissue along the tissue seal.

In still another embodiment, the electrode is recessed within an inner peripheral surface of the ring-like snare and includes a cutting edge that deploys when the ring-like snare is cinched beyond a predetermined sealing pressure of about 16 kg/cm$^2$.

The present disclosure also relates to a method for performing a laparoscopic hysterectomy and includes the initial step of providing a uterine manipulator having a shaft having a handle at a proximal end thereof operable by a user and an operating end at a distal end thereof manipulatable by the handle to orient and position tissue. The method also includes the step of providing a uterine sealer having a shaft with a handle disposed at a proximal end thereof and a ring-like snare disposed at a distal end thereof having a diameter. The handle includes an actuator operably associated therewith which selectively cinches and expands the diameter of the snare. The uterine manipulator and/or the uterine sealer includes an electrode disposed at the distal end thereof.

The method also includes the steps of: inserting the uterine manipulator into a body cavity to engage and manipulate tissue; inserting the uterine sealer into a second body cavity to encircle the tissue being manipulated by the uterine manipulator; activating the actuator to cinch the diameter of the snare to engage tissue between the operating end of the uterine manipulator and the snare; energizing the electrode to seal tissue disposed between the operating end of the uterine manipulator and the snare; and resecting the tissue along the tissue seal and removing the resected tissue from the body cavity.

In one embodiment according to one particular method, the tissue is engaged between the operating end of the uterine manipulator and the snare under a working pressure of about 3 kg/cm$^2$ to about 16 kg/cm$^2$. In one method, the uterine sealer includes the electrode that cooperates with a return electrode located remotely from the operating cavities to seal tissue while in another method both the uterine sealer and the uterine manipulator include electrodes which mutually cooperate in a bipolar fashion to seal tissue.

The method may additionally or alternatively include the step of further manipulating the uterine sealer and/or uterine manipulator to resect tissue along the tissue seal by energizing a cutting electrode disposed on the uterine sealer and/or uterine manipulator. The cutting electrode and the sealing electrode disposed on the uterine sealer (or the uterine manipulator) may be one in the same.

The method may additionally or alternatively include the step of further manipulating the uterine sealer and/or uterine manipulator to resect tissue along the tissue seal by mechanically deploying a tissue cutter to resect tissue along the tissue seal.

The present disclosure also relates to a method for performing a laparoscopic hysterectomy including the steps of:
 providing a uterine manipulator having a shaft including a handle at a proximal end thereof operable by a user and an operating end at a distal end thereof manipulatable by the handle to orient and position tissue;
 providing a uterine sealer including a shaft having a handle disposed at a proximal end thereof and a ring-like snare disposed at a distal end thereof having a diameter, the handle including an actuator operably associated therewith which selectively cinches and expands the diameter of the snare, the uterine sealer including an electrode disposed at the distal end thereof, the electrode including a sharpened edge;
 inserting the uterine manipulator into a body cavity to engage and manipulate tissue;
 inserting the uterine sealer into a second body cavity to encircle the tissue being manipulated by the uterine manipulator;
 activating the actuator to cinch the diameter of the snare to engage tissue between the operating end of the uterine manipulator and the snare under a sealing pressure;
 energizing the electrode to seal tissue disposed between the operating end of the uterine manipulator and the snare;
 further cinching the diameter of the snare beyond the sealing pressure to deploy the sharpened edge of the electrode to resect tissue; and
 removing the resected tissue from the body cavity.

In one particular method, the uterine sealer of the providing step includes an inner peripheral surface that includes the electrode recessed therein. The electrode is selectively deployable beyond the inner peripheral surface to resect tissue when the cinching pressure of the snare on the tissue is beyond the sealing pressure of about 16 kg/cm². The electrode may be energized during the step of further cinching the snare to facilitate resecting the tissue.

BRIEF DESCRIPTION OF THE DRAWINGS

Various particular embodiments of the presently disclosed systems, devices and methods are disclosed herein with reference to the drawings wherein.

DETAILED DESCRIPTION

Figure 1:
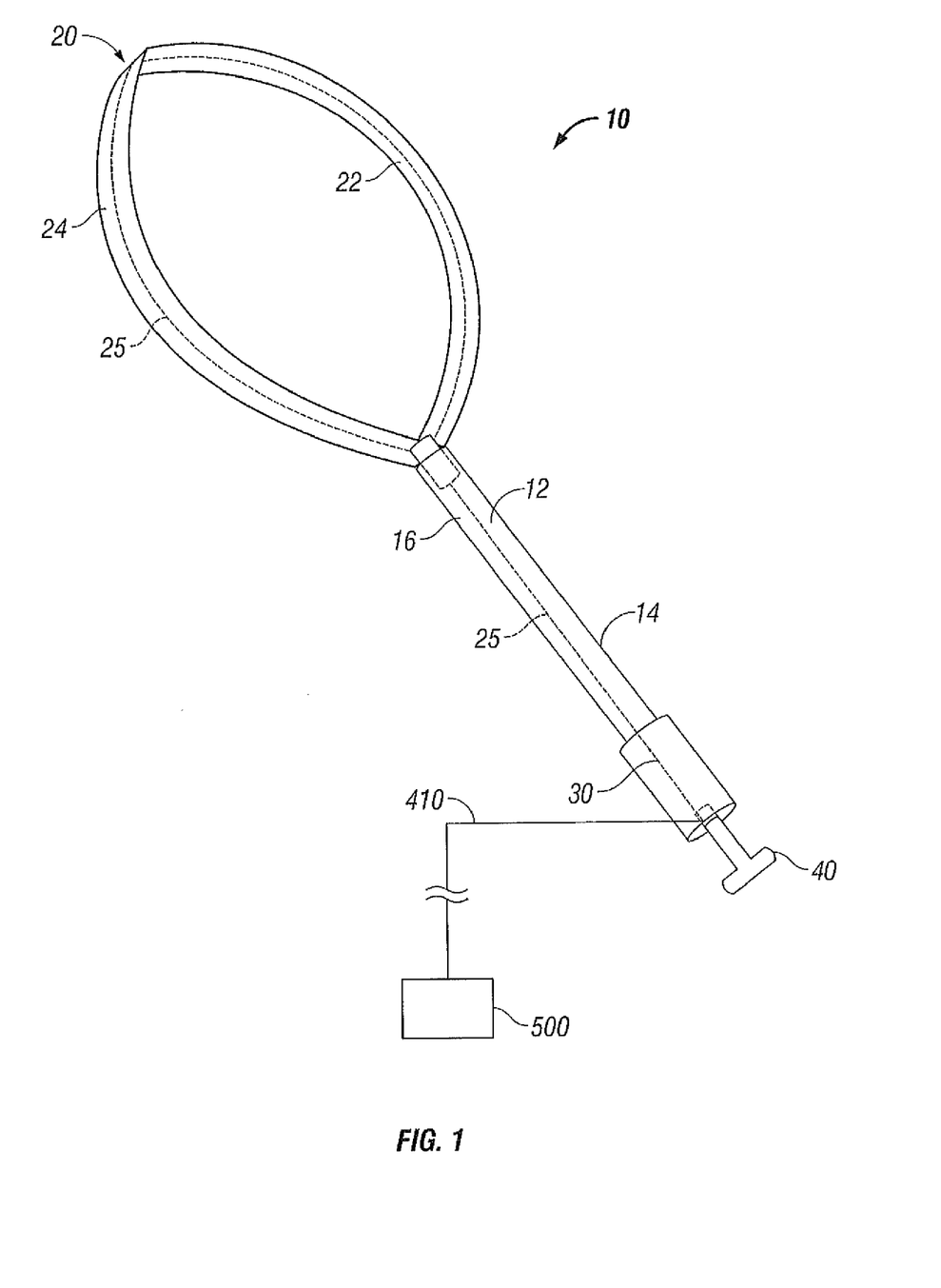
FIG. 1 is a schematic representation of a uterine sealer having a ring-like operative end according to an embodiment of the present invention.

Referring initially to FIG. 1, one embodiment of a uterine sealer is shown and is generally designated as sealer 10. Sealer 10 includes a generally elongated shaft 12 having proximal and distal ends 14 and 16, respectively. The distal end 16 of the shaft 12 is configured to support a loop-like or ring-like snare or cinch 20 and the proximal end 14 of the shaft 12 is operatively coupled to a handle 30. The shaft 12 may be pliable or semi-rigid to facilitate positioning of the sealer 10 within an operating cavity 80 (See FIG. 3B). More particularly, the shaft 12 may be selectively bendable, rotatable, articulatable or otherwise positionable to orient the ring-like snare 20 about a target organ, e.g., cervix 320 (See FIGS. 3A-3E). Shaft 12 may also be telescopic (not shown), which may prove particular useful for certain surgical purposes. In view thereof, handle 30 may be configured to include one or more actuators (not shown) that are actuatable to orient the ring-like snare 20 relative to a target organ for ensnarement, as will be explained in more detail below with reference to FIGS. 3A-3E.

Handle 30 also includes an actuator 40 that operatively couples to a control cable 25 internally disposed within shaft 12 and ring-like snare 20. Actuator 40 is configured to reciprocate cable 25 from a first position wherein the cable 25 expands the ring-like snare 20 to a fully open configuration (as shown) to a subsequent or second position that reduces the diameter of the snare 20 such that an inner peripheral surface 22 of the snare 20 grasps and encircles target tissue (See FIG. 3C). Actuator 40 may be configured as a pull knob (as shown) which biases against handle 30 to reciprocate cable 25 or any other suitable type of actuator that is designed to reciprocate a cable 25, e.g., a lever-like actuator, a rotational actuator, an electrical or mechanical winch-like actuator, etc.

As described in detail below with reference to FIGS. 3A-3E, the cable 25 may be configured to act as an electrode and coupled to an electrosurgical energy source, such as an electrical generator 500. In this configuration, the cable 25 may conduct a sealing current therethrough that acts as one pole of a bipolar or monopolar sealing system. Moreover, and again as explained in more detail below, the cable 25 may also operatively communicate with the generator 500 to generate a cutting current to resect the target tissue once sealed. In another embodiment, the cable 25 is configured as a mechanical cutter to resect tissue once the seal is completed, as discussed below with reference to FIGS. 4A-4D.

Figure 2:
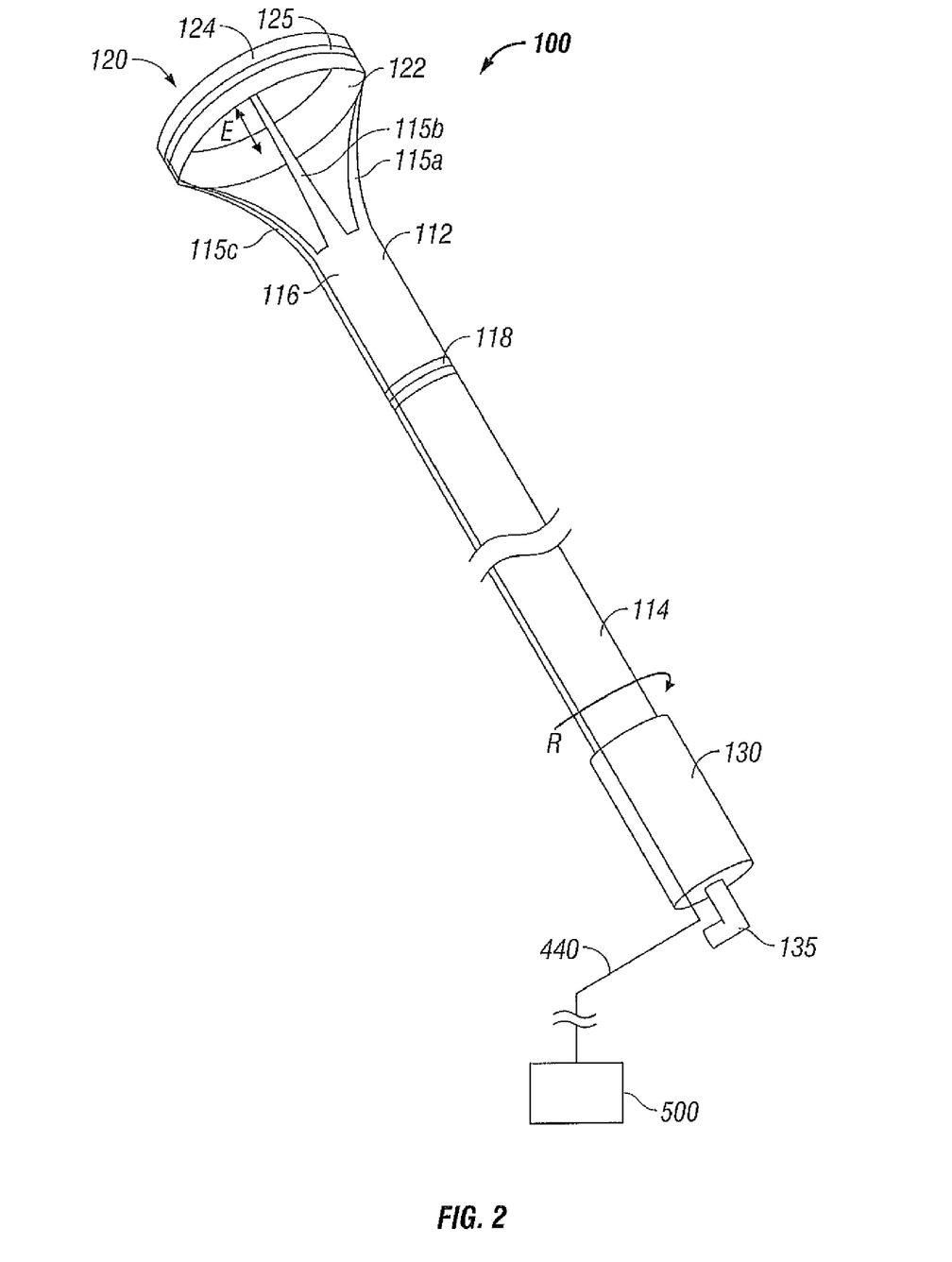
FIG. 2 is a schematic illustration of a uterine manipulator for use with the uterine sealer of FIG. 1.

FIG. 2 shows one embodiment of a uterine manipulator 100 for use in manipulating and positioning the organs of the uterus "U" and tissue for surgical purposes, e.g., tubal ligations; removal or partial removal of the uterus, fallopian tubes and ovaries; laparoscopic hysterectomy and other surgeries. Uterine manipulator 100 includes a generally elongated shaft 112 having proximal and distal ends 114 and 116, respectively, and a selectively expandable ring or cuff 120 disposed at the distal end 116 having an outer peripheral surface 124 that is configured to engage tissue for manipulation purposes. Shaft 112 may include one or more hinges 118 configured to allow rotation, pivoting or articulation of the shaft 112 for manipulation purposes.

The proximal end 114 of the shaft 112 includes a handle 130 that allows a user to orient the manipulator 100 within a vaginal cavity 310 (see FIG. 3A) to position and reposition tissue as needed during the surgical procedure. Handle 130 may be equipped with one or more actuators 135 that facilitate rotation, articulation and/or positioning of the manipulator 100 within the vaginal and cervical cavities 310 and 322, respectively. The manipulator may be inserted within other cavities depending upon particular surgical purposes or to manipulate other organs, e.g., anal cavity 315. Moreover, the actuator 135 may further facilitate positioning of the manipulator 100 to operatively engage the sealer 10 as described in more detail below.

As mentioned above, the distal end 116 of shaft 112 includes a cuff of ring 120 that is selectively expandable from a first, collapsed configuration for insertion purposes to a second expanded configuration (See FIG. 2) for engaging and manipulating tissue. The distal end 116 includes a series of finger-like projections 115a-115c that support the cuff 120 for manipulation purposes. Handle 130 may be configured to rotate in the direction of arrow "R" from a first position that maintains the cuff 120 in a collapsed configuration to a second configuration that expands the cuff 120 in the expanded configuration "E" (and vice versa) for manipulation and sealing purposes (See FIG. 3C). The handle 130 may also be configured to lock the cuff 120 in an expanded configuration with enough force to oppose an electrode, e.g., electrode 25 of the uterine sealer 10, for sealing and cutting tissue, as explained in more detail below. An inner peripheral surface 122 of the cuff 120 may be configured from a semi-rigid material, include struts, scaffolding or support structure (not shown) to accomplish this purpose.

The outer peripheral surface 124 of the cuff 120 supports an electrode 125 therealong that is configured to act both as a support structure for maintaining the integrity of the cuff 120 when expanded and to act as one pole during a bipolar sealing process or a monopolar sealing process, as explained in more detail below. Moreover, the electrode 125 may be configured to produce a cutting current to cut tissue along the tissue seal after the sealing process is complete which is also explained in more detail below. As such, the electrode 125 is connected to the electrosurgical generator 500 by a lead 440 running through manipulator 100 and coupled to the generator 500.

Electrosurgical generator 500 may be a radiofrequency or high frequency type generator and include control elements that may, for example, increase the radiofrequency power output of electrodes 25 and/or 125 and control other operating parameters to regulate the sealing and/or cutting of cervical or uterine tissue. The generator may be operatively associated with one or more suitable controls or sensors (not shown) mounted to or operatively associated with the uterine manipulator 100 or uterine sealer 10 that monitor or control impedance, temperature, power, current, voltage, or other suitable output parameters. Electrosurgical generator 500 may include a display or screen therein or as a separate system for providing a display of parameters, such as temperature, impedance, power, current, or voltage of the radiofrequency output.

Moreover, generator 500 may include a first sealing algorithm that regulates, monitors or otherwise controls the sealing cycle and a second algorithm that regulates or controls the cutting cycle. More particularly, the generator 500 may include a first algorithm that controls electrode 25 and/or electrode 125 to regulate the electrosurgical energy to effect a tissue seal. Vessel sealing or tissue sealing utilizes a unique combination of radiofrequency energy, pressure and gap control to effectively seal or fuse tissue between two opposing sealing electrodes. Vessel or tissue sealing is more than "cauterization" that involves the use of heat to destroy tissue (also called "diathermy" or "electrodiathermy"). Vessel sealing is also more than "coagulation", which is the process of desiccating tissue wherein the tissue cells are ruptured and dried. "Vessel sealing" is defined as the process of liquefying the collagen, elastin and ground substances in the tissue so that the tissue reforms into a fused mass with significantly-reduced demarcation between the opposing tissue structures.

The generator 500 also includes a second algorithm that controls one or both electrodes 25 and/or 125 to effect a tissue cut. For example, the tissue cut may be produced by one electrode, e.g., electrode 25, producing a first electrical potential having a cutting effect through the tissue which is returned by a return electrode 600 placed remotely under the patient skin (See FIG. 3E). Alternatively, electrode 125 may act as the return electrode when electrode 25 is the cutting electrode and produces a cutting effect. Alternatively, electrode 125 may also act as a cutting electrode and electrode 25 may also act as a return electrode or the generator may be configured to alternate between electrodes 25 and 125 during the cutting process to produce a particular cutting effect.

A safety switch or circuit (not shown) may be included with the generator 500 such that the electrodes 25 and 125 cannot activate to initiate a seal or a cut unless there is tissue disposed therebetween, e.g., a sensor (not shown) may be employed to determine if tissue is held therebetween. Obviously, this would insure proper placement of the sealer and the manipulator prior to activation.

Figure 3A:
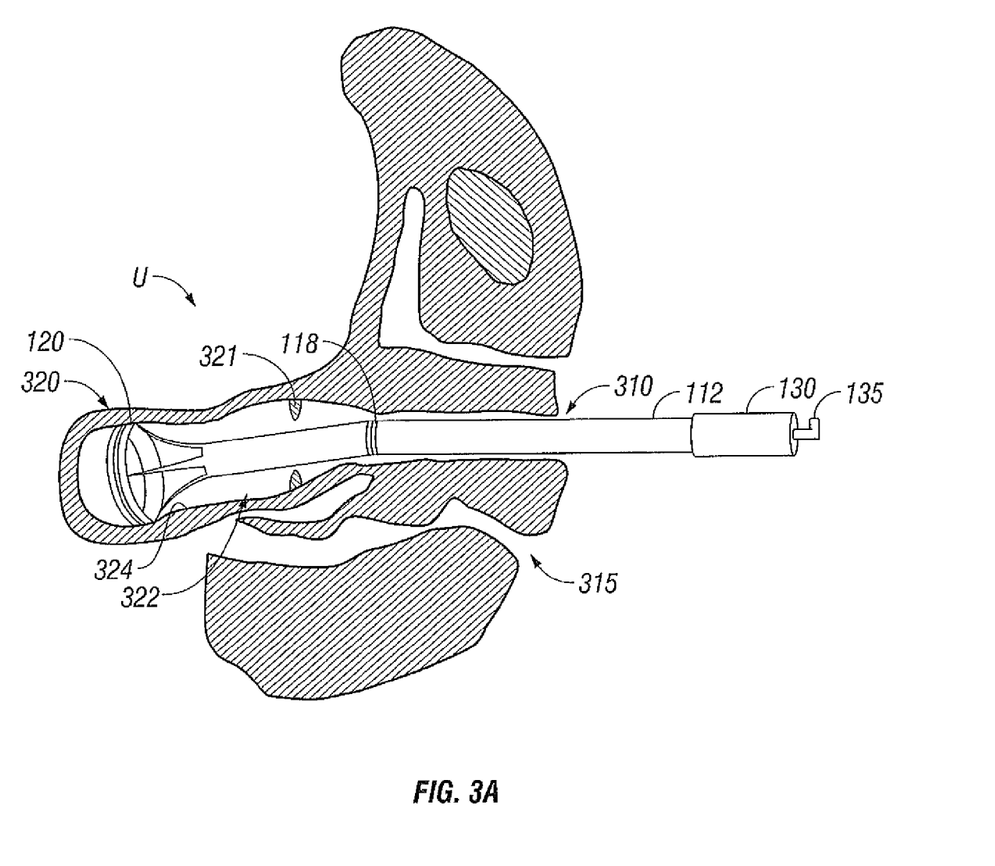
FIGS. 3A-3E are internal schematic illustrations of the uterine sealer and uterine manipulator being used to perform a laparoscopic hysterectomy.

FIGS. 3A-3E show an intended use of the uterine manipulator 100 and uterine sealer 10 during a laparoscopic hysterectomy or partial hysterectomy. More particularly, and as best shown in FIG. 3A, the cuff 120 of the uterine manipulator 100 is inserted into the vaginal cavity 310 in a collapsed configuration and manipulated into position to engage the opening 321 of the cervix 320. Once engaged, the cuff 120 of the manipulator 100 is inserted into the opening 321 of the cervix 320 and the handle 130 is rotated in the direction "R" to expand the cuff 120 in the direction "E" within the cervix 320 to exert internal pressure against the internal walls 324 of the cervix 320. Actuator 135 is then used to orient the cervix 320 into any desired position "M" about hinge 118 for cooperative engagement with sealer 10, as described below.

Figure 3B:
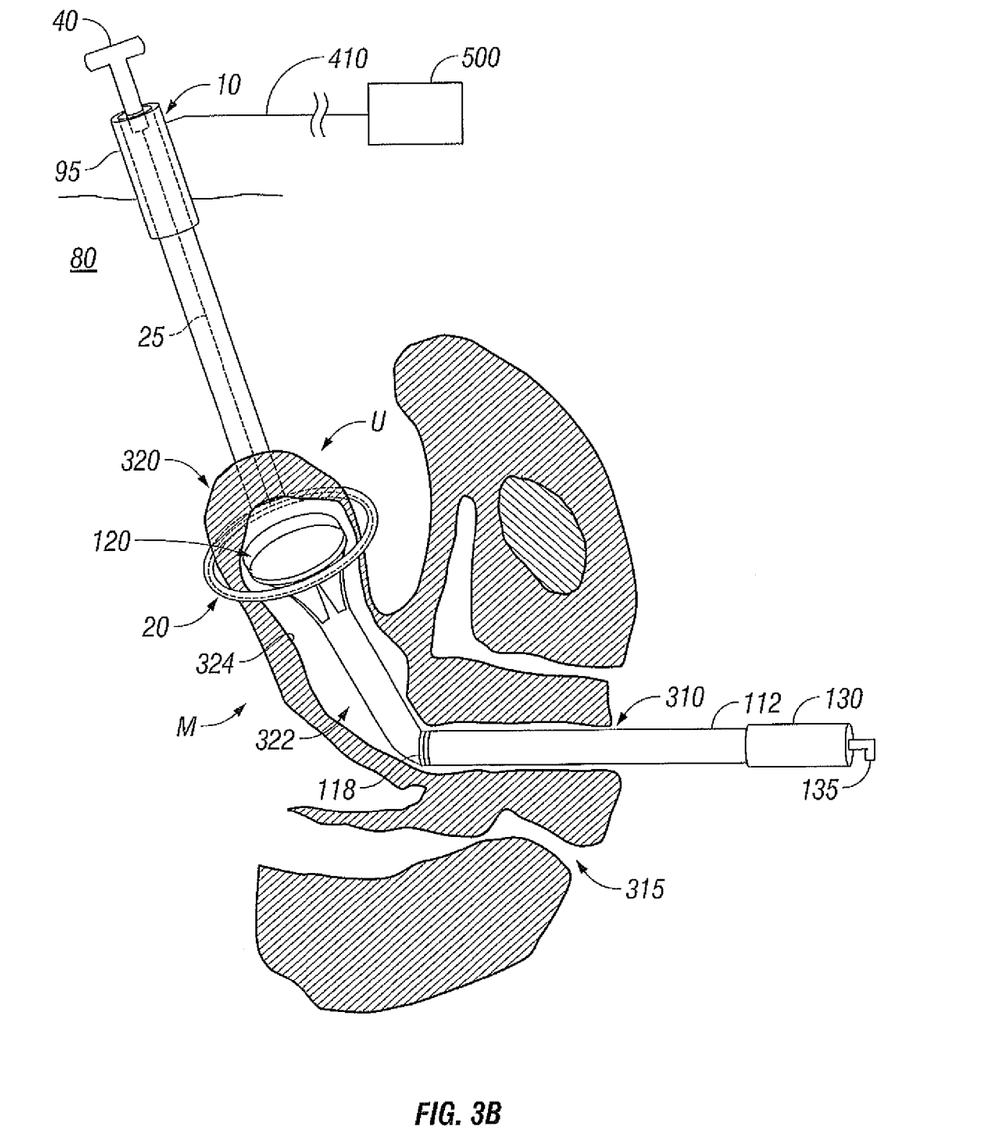
Figure 3C:
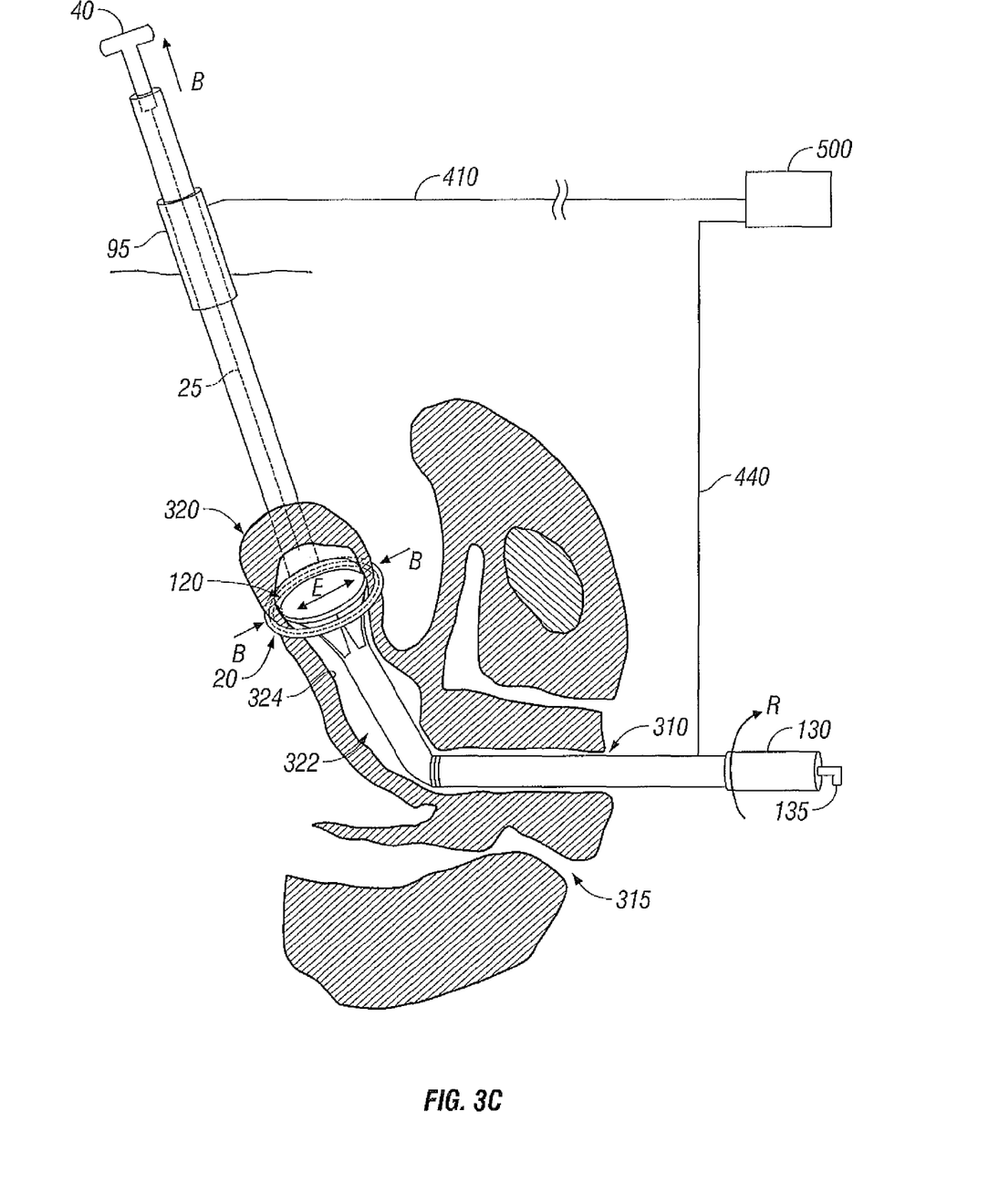

As shown in FIG. 3B, sealer 10 is inserted through a trocar 95 into a surgical cavity 80 made above the cervix 320 with the snare 20 in a collapsed configuration and then the snare 20 is expanded to encircle the cervix 320. The user then manipulates the sealer 10 to encircle the cervix 320. Actuator 40 is then activated to cinch snare 20 (e.g., reduce the diameter of snare 20) and engage cuff 120 with cervical tissue disposed between snare 20 and cuff 120. Prior to exerting the pressure required to produce a proper seal, the cuff 120 and snare 20 may be slid atop the cervix 320 to the proper or desired position or repositioned atop the cervix 320 by reducing the diameter of the cuff 120 or expanding the diameter of the snare 20. For example, the desired position may be at the vaginal-cervico junction, the utero-cervico junction, or other suitable location. Once the proper position is located for sealing purposes, the snare 20 is cinched in the direction "B" via actuator 40 against the internal pressure "E" of the cuff 120 and electrosurgical energy is applied to electrodes 25 and/or 125 of the snare 20 and cuff 120, respectively (See FIG. 3C).

Figure 3D:
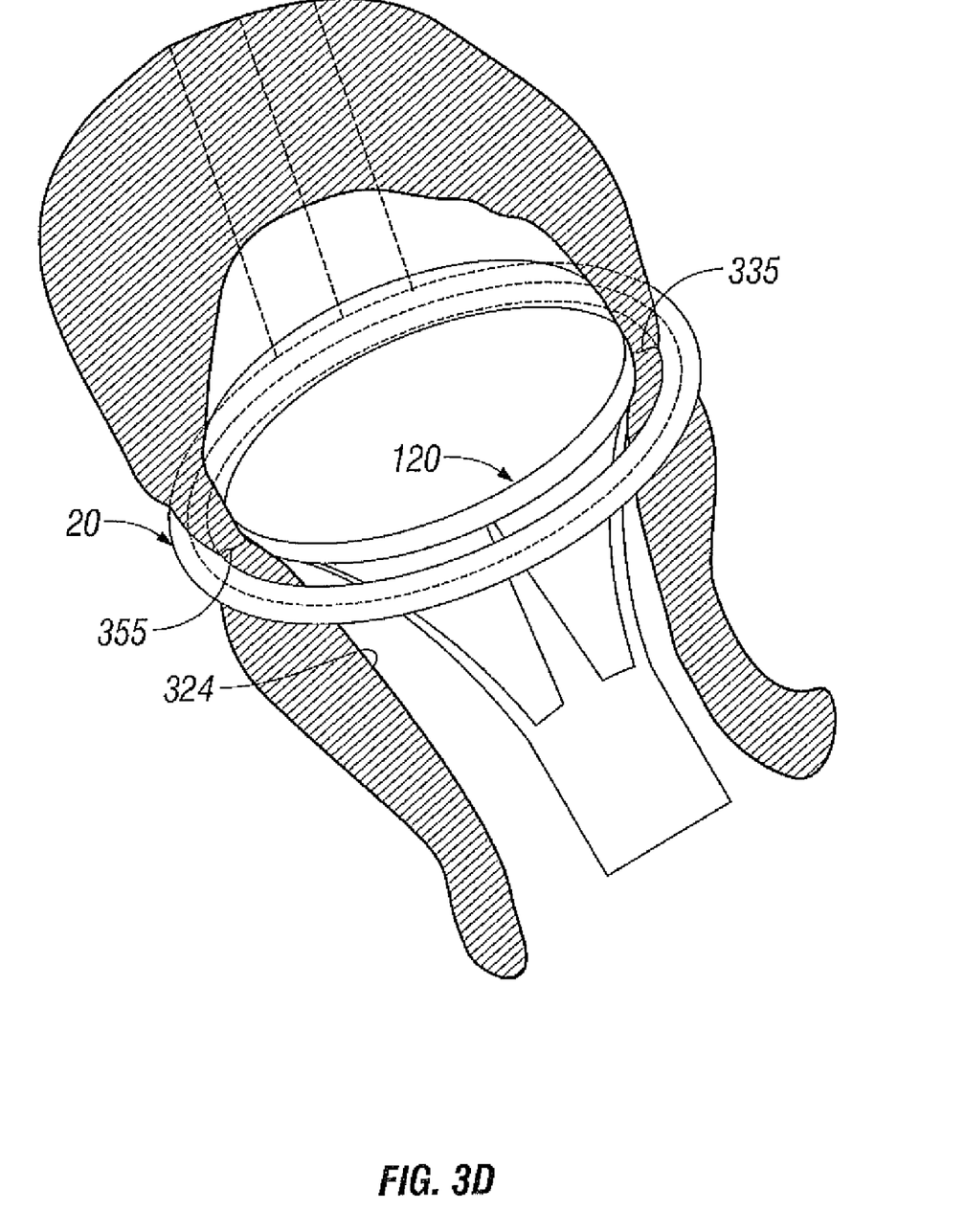

Any suitable working pressure may be utilized; however, in one embodiment, a working pressure of about 3 kg/cm² to about 16 kg/cm² is utilized to effect a proper seal 355 (See FIG. 3D). The duration or activation time to effect a seal is dependent on the thickness of the cervical tissue 320 that may be measured by one or more suitable sensors (not shown) coupled to the sealer 10 or the manipulator 100 or may be determined when a threshold impedance is reached (measured by the generator 500). It is important to note that the seal 355 (See FIG. 3E) may be created by activating both electrodes 25 and 125 in a bipolar fashion under the appropriate working pressure or alternatively by activating one electrode 25 or 125 and a remote return electrode (e.g., a return pad 600 (See FIG. 3E) in a monopolar fashion).

Figure 3E:
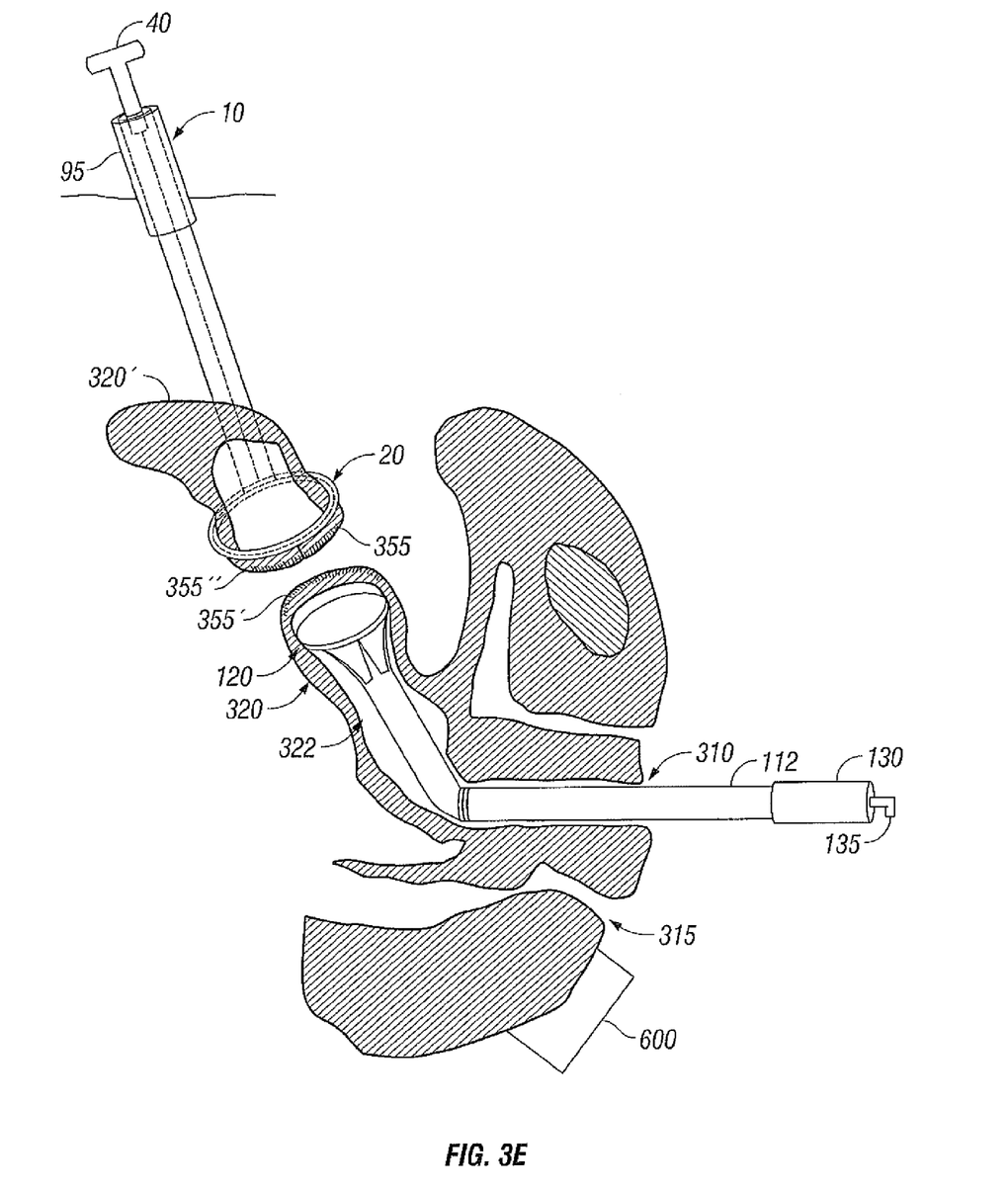

Once electrosurgical energy is applied to electrode 25 and 125 via generator 500 under the appropriate working pressure to produce seal 355, the cervical tissue 320 may be resected along the seal plane 355 either mechanically, electrically or electromechanically. For example, and as shown in FIG. 3E, the generator 500 may be configured to produce a cutting algorithm that generates a cutting current to one or both electrodes 25 and/or 125 to cut the tissue along the tissue seal 355 into two distinct sealed sections 355' and 355" with little or no bleeding.

The cutting current is typically a higher intensity current than the sealing current. In one particular embodiment, only one electrode, e.g., the smaller width electrode, which may be either 25 or 125 depending on a particular configuration, produces the cutting effect, while the other electrode acts as the return electrode.

Figures 4A, 4B:
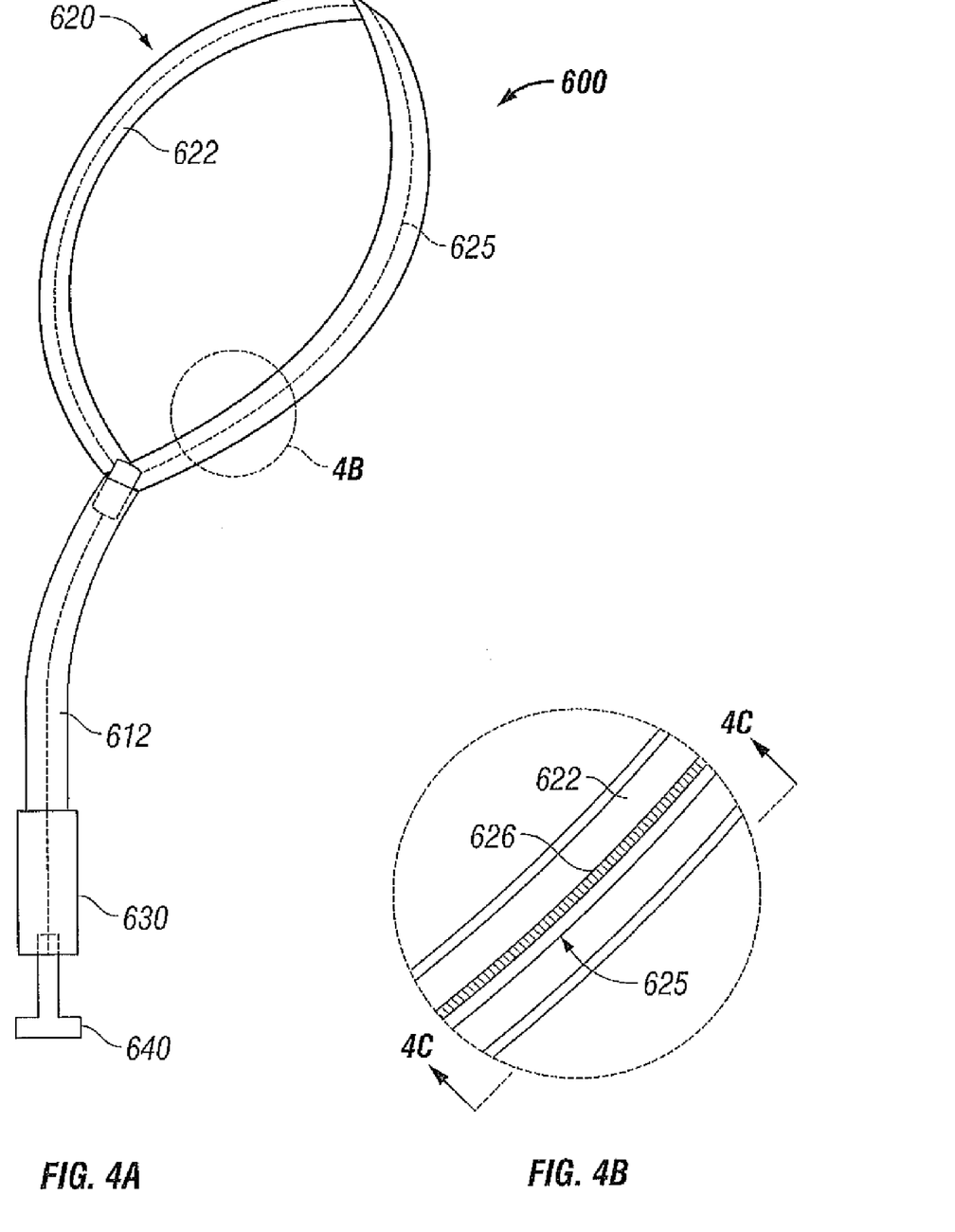
FIG. 4A is a schematic view of another embodiment of a uterine sealer according to the present disclosure having a mechanical cutting blade internally disposed within the inner peripheral surface of the ring-like operative end.
FIG. 4B is an enlarged view of the area of detail of FIG. 4A.
Figure 4C:
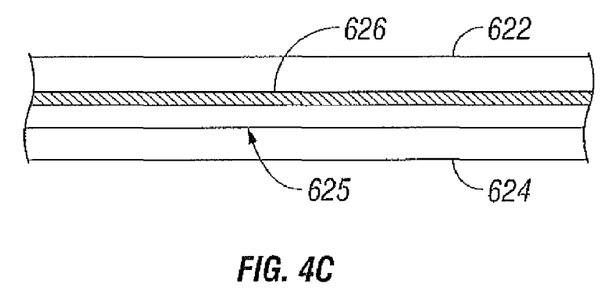
FIG. 4C is a side, cross-sectional view of the ring-like operative end prior to advancement of the cutting blade through the inner peripheral surface thereof.

In another embodiment, and as best shown in FIGS. 4A and 4B, a uterine sealer 600 includes a snare having a mechanical cutter 625 disposed therein. More particularly, sealer 600 acts in a similar fashion as sealer 10 and includes shaft 612 having handle 630 and actuator 640 that operates snare 620 to cinch tissue for laparoscopic hysterectomies. An electrode 625 is disposed along the inner peripheral surface 622 of snare 620 and is selectively activatable to seal tissue to create a tissue seal 355 in much the same fashion as described above with respect to FIGS. 3A-3E. Electrode 625 includes a sharpened distal edge 626 that during the sealing cycle and under the working sealing pressure remains recessed beneath the inner working surface of the snare 620, as best shown in FIG. 4C.

Figure 4D:
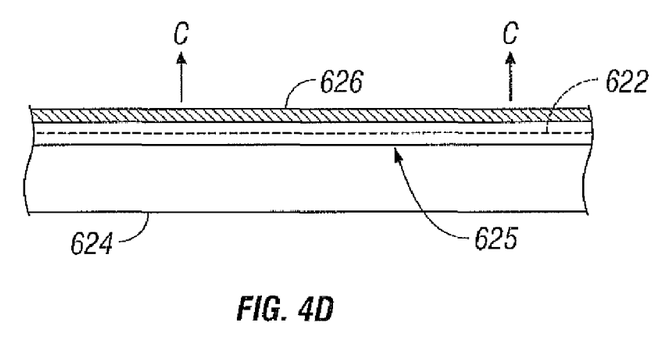
FIG. 4D is a side cross-sectional view of the ring-like operative end after advancement of the cutting blade through the inner peripheral surface thereof.

During the cutting phase of the laparoscopic hysterectomy, the surgeon exerts a greater cinching pressure beyond the working pressure that causes the sharpened edge 626 of the electrode 625 to pierce the inner working surface 622 of the snare 620 in the direction of arrows "C" and cut the cervical tissue 320 along the seal 355 (See FIG. 4D). In an alternative embodiment, the electrode 625 may be electrified to facilitate cutting the cervical tissue 320 depending upon a particular surgical purpose.

Figure 5:
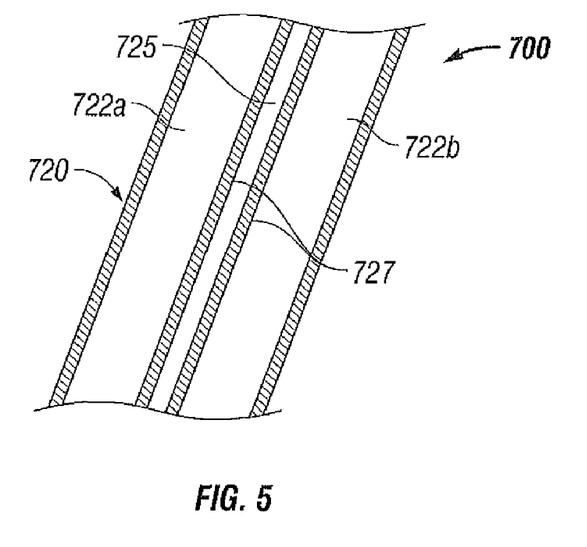
FIG. 5 is a schematic view of another embodiment of a uterine sealer according to the present disclosure configured to include an electrical sealing and cutting electrode disposed on the face of the inner peripheral surface of the ring-like operative end.

FIG. 5 shows an alternate embodiment of a uterine sealer 700 having an electrical sealing and/or cutting electrode 725 for use with a snare 720. The snare 720 includes an insulator 727 disposed on either side of the electrode 725 thereby separating the inner peripheral surface into rings 722a and 722b. The insulator 727 is configured to isolate electrosurgical current during the sealing and cutting stages to enhance the electrosurgical effect on the cervical tissue 320.

The present disclosure also relates to a method of performing a laparoscopic hysterectomy (partial or otherwise) and includes the initial step of providing a uterine manipulator 100 having a shaft 112 including a handle 130 at a proximal end thereof operable by a user and an operating end 120 at a distal end thereof manipulatable by the handle 130 to orient and position tissue.

The method also includes the steps of providing a uterine sealer 10 including a shaft 12 having a handle 30 disposed at a proximal end thereof and a ring-like snare 20 disposed at a distal end thereof, the handle 30 including an actuator 40 operably associated therewith which selectively cinches and expands the diameter of the snare 20. The uterine manipulator 100 and/or the uterine sealer 10 include one or more electrodes 125, 25, respectively, disposed at the distal end thereof that are configured to cooperate to seal tissue, as explained in more detail below.

The method also includes the steps of: inserting the uterine manipulator 100 into a body cavity 310 to engage and manipulate tissue 320 and inserting the uterine sealer 10 into a second body cavity 80 to encircle the tissue 320 being manipulated by the uterine manipulator 100. Further, the method includes the steps of: activating the actuator 40 to cinch the snare 20 to engage tissue 320 between the distal end of the uterine manipulator 100 and the snare 20 under a working pressure of about 3 kg/cm² to about 16 kg/cm²; energizing the electrode(s) 125 and/or 25 to seal tissue disposed between the distal end of the uterine manipulator 100 and the snare 20; and resecting the tissue 320 along the tissue seal 355 and removing the resected tissue 320' from the body cavity 80.

Both the uterine sealer 10 and the uterine manipulator 100 may include electrodes 25 and 125, respectively, that mutually cooperate in a bipolar fashion to seal tissue. The method may further include the step of manipulating the uterine sealer 700 and/or the uterine manipulator 100 to resect tissue along the tissue seal by energizing a cutting electrode 725 disposed on the uterine sealer 700 and/or uterine manipulator 100 or mechanically deploying a tissue cutter 625 to resect tissue along the tissue seal.

The present disclosure also relates to a method for performing a laparoscopic hysterectomy including the steps of providing a uterine manipulator 100 having a shaft 112 having a handle 130 at a proximal end thereof operable by a user and an operating end or cuff 120 at a distal end thereof manipulatable by the handle 110 to orient and position tissue. The method also includes the steps of providing a uterine sealer 600 having a shaft 612 with a handle 630 disposed at a proximal end thereof and a ring-like snare 620 disposed at a distal end thereof. The handle 630 includes an actuator 640 operably associated therewith which selectively cinches and expands the diameter of the snare 620. The uterine sealer 610 includes an electrode 625 disposed at the distal end thereof with a sharpened cutting edge 626.

The method further includes the steps of inserting the uterine manipulator 100 into a body cavity 310 to engage and manipulate tissue 320 and inserting the uterine sealer 600 into a second body cavity 80 to encircle the tissue 320 that is being manipulated by the uterine manipulator 100. The method further includes the steps of: activating the actuator 640 to cinch the snare 640 to engage tissue 320 between the distal end of the uterine manipulator 100 and the snare 640 under a sealing pressure and energizing the electrode 625 to seal tissue 320 disposed between the distal end 120 of the uterine manipulator 100 and the snare 620; further cinching the snare 620 of the uterine sealer 600 beyond the sealing pressure (e.g., about 16 kg/cm²) to deploy the sharpened edge 626 of the electrode 625 to resect uterine tissue 320; and removing the resected tissue 320' from the body cavity 80.

From the foregoing and with reference to the various figure drawings, those skilled in the art will appreciate that certain modifications can also be made to the present disclosure without departing from the scope of the same. For example, variations in the choice of electrical output parameters from the electrosurgical generator 500 to control or monitor the sealing and cutting processes may vary widely depending on the operator's experience, technique, or preference.

Moreover, certain aspects of the sealing process may be automatically controlled and regulated by the generator, e.g., the, current, voltage, duration, and other output parameters to optimize the sealing process and produce a reliable and effective tissue seal. Still further, the generator may control certain aspects of the cutting process and may selectively regulate the cutting electrodes to optimize the cutting effect depending on tissue type, tissue thickness, type of surgical procedure or desired surgical effect.

It is contemplated that the uterine sealer 10, 600, 700 may be equipped with both the sealing and cutting electrodes and, as a result, may be utilized with any conventional uterine manipulator 100 and achieve the same desired surgical effect as described herein above. In this instance, it may be necessary to utilize one or more return electrodes (not shown) that operably couple to the generator 500 for the sealing and/or cutting processes. In one embodiment, the shaft 12 and/or 112 of the sealer 10 and/or the manipulator 100, respectively, may be telescopically adjustable to facilitate positioning relative to one or more internal organs.

While various embodiments of the disclosure have been described, it is not intended that the disclosure be limited thereto, as it is intended that the disclosure be as broad in scope as the art will allow and that the specification be read likewise. Therefore, the above descriptions should not be construed as limiting, but merely as exemplifications of particular embodiments. Those skilled in the art will envision other modifications within the scope and spirit of the claims appended hereto.

What is claimed is:

1. A method for performing a laparoscopic hysterectomy comprising the steps of:
    inserting a uterine manipulator into a body cavity to engage tissue;
    inserting a second uterine sealer instrument having a snare into a second body cavity to encircle the tissue;
    cinching a diameter of the snare of the uterine sealer to engage the tissue between an operating end of the uterine manipulator and the snare of the uterine sealer;
    energizing an electrode associated with one of the uterine manipulator and uterine sealer; and
    resecting the tissue along the tissue seal.

2. A method according to claim 1 wherein the tissue is engaged between the operating end of the uterine manipulator and the snare of the uterine sealer under a working pressure of about 3 kg/cm2 to about 16 kg/cm2.

3. A method according to claim 1 wherein the uterine sealer includes the electrode that cooperates with a return electrode located remotely from the operating cavities to seal tissue.

4. A method according to claim 1 wherein the uterine sealer includes a first electrode and the uterine manipulator includes a second electrode that mutually cooperate in a bipolar fashion to seal tissue.

5. A method according to claim 1, wherein resecting the tissue along the tissue seal includes the step of:
    further manipulating one of the uterine sealer and uterine manipulator to resect tissue along the tissue seal.

6. A method according to claim 5 wherein the step of further manipulating one of the uterine sealer and uterine manipulator to resect tissue along the tissue seal includes energizing a cutting electrode disposed on one of the uterine sealer and uterine manipulator.

7. A method according to claim 6 wherein the cutting electrode and the sealing electrode disposed on at least one of the uterine sealer and the uterine manipulator are one in the same.

8. A method according to claim 6 wherein the step of further manipulating one of the uterine sealer and uterine manipulator to resect tissue along the tissue seal includes mechanically deploying a tissue cutter to resect tissue along the tissue seal.

9. A method for performing a laparoscopic hysterectomy comprising the steps of:
    inserting a uterine manipulator into a body cavity to engage tissue;
    inserting a second uterine sealer instrument having a snare into a second body cavity to encircle the tissue;
    cinching a diameter of the snare of the uterine sealer to engage the tissue between an operating end of the uterine manipulator and the snare of the uterine sealer under a sealing pressure;
    energizing an electrode associated with the uterine sealer to seal tissue disposed between the uterine manipulator and the snare of the uterine sealer, the electrode of the uterine sealer including a sharpened edge; and
    further cinching the diameter of the snare of the uterine sealer beyond the sealing pressure to deploy the sharpened edge of the electrode of the uterine sealer to resect the tissue.

10. A method according to claim 9 wherein the sealing pressure is about 3 kg/cm2 to about 16 kg/cm2.

11. A method according to claim 9 wherein the uterine sealer includes an inner peripheral surface that includes the electrode recessed therein, the electrode of the uterine sealer being selectively deployable beyond the inner peripheral surface to resect tissue when the cinching pressure of the snare of the uterine sealer on the tissue is beyond the sealing pressure.

12. A method according to claim 11 wherein the electrode of the uterine sealer is energized during the step of further cinching the snare of the uterine sealer to facilitate resecting the tissue.

13. A uterine sealer device for use with an operating end of a uterine manipulator for sealing uterine tissue, comprising:
    a shaft having a handle at an operating end thereof and a ring-like snare at a distal end thereof, the handle including an actuator operable to selectively cinch the ring-like snare from a first configuration having a first diameter to at least one subsequent configuration having a second diameter; and
    an electrode operably coupled to an inner peripheral surface of the ring-like snare, the electrode adapted to connect to an electrical energy source to energize uterine tissue to create a tissue seal;
    wherein the shaft is selectively positionable within a surgical cavity such that the ring-like snare encircles uterine tissue and operably engages and cinches the operating end of the uterine manipulator under a sealing pressure while electrosurgical energy is applied to the electrode to seal the uterine tissue disposed between the uterine manipulator and the ring-like snare of the uterine sealer.

14. A uterine sealer according to claim 13 wherein the uterine sealer device includes a second electrode that is adapted to connect to the electrical energy source, the second electrode of the uterine sealer being energized after the completion of the uterine tissue seal to resect the uterine tissue along the tissue seal.

15. A uterine sealer according to claim 14 wherein the electrode of the uterine sealer is further energized after the completion of the uterine tissue seal to resect the uterine tissue along the uterine tissue seal.

16. A uterine sealer according to claim 14 wherein the electrode of the uterine sealer is recessed within an inner peripheral surface of the ring-like snare of the uterine sealer and includes a cutting edge that deploys when the ring-like snare is cinched beyond a predetermined sealing pressure.

17. A uterine sealer according to claim 16 wherein the sealing pressure is about 3 kg/cm2 to about 16 kg/cm2.

18. A system for performing a laparoscopic hysterectomy, comprising:
- a uterine manipulator configured for insertion into a body cavity and configured to operatively engage uterine tissue;
- a second uterine sealer instrument configured for insertion into a second body cavity, the uterine sealer including a snare having a diameter selectively;
- wherein the diameter of the snare of the uterine sealer is selectively actuatable to encircle uterine tissue and selectively cinchable to engage tissue between an operating end of the uterine manipulator and the diameter of the snare of the uterine sealer; and
- wherein at least one of the uterine manipulator and uterine sealer includes an electrode adapted to couple to an electrosurgical generator, the generator being selectively energizable to at least one of seal and resect tissue disposed between the operating end of the uterine manipulator and the diameter of the snare of the uterine sealer.

19. A system according to claim 18 wherein the tissue disposed between the operating end of the uterine manipulator and the snare of the uterine sealer is engaged under a working pressure of about 3 kg/cm2 to about 16 kg/cm2 which effectively seals the tissue upon activation of the electrode of at least one of the uterine manipulator and uterine sealer.

* * * * *